United States Patent [19]

Donovan

[11] Patent Number: 4,581,754
[45] Date of Patent: Apr. 8, 1986

[54] RADIOGRAPHIC RACK APPARATUS FOR ANIMALS

[76] Inventor: Timothy J. Donovan, P.O. Box 465, Norton, Mass. 02766

[21] Appl. No.: 568,076

[22] Filed: Jan. 5, 1984

[51] Int. Cl.⁴ .................. H05G 1/00; G03B 42/02
[52] U.S. Cl. ............................ 378/208; 378/177; 128/133; 128/134; 119/96; 119/103
[58] Field of Search ............ 378/180, 208, 177; 128/133, 134; 119/96, 103

[56] References Cited

U.S. PATENT DOCUMENTS 2,708,422  5/1955  Morrison ........................ 119/103
4,321,890  3/1982  Lange et al. ..................... 128/133

Primary Examiner—Richard L. Schilling
Attorney, Agent, or Firm—John A. Haug

[57] ABSTRACT

A rack of radiographically transparent material for positioning and restraining animals such as dogs and cats during radiographical procedures is shown to include converging load support walls to wedge an animal in either a ventro dorsal or dorso ventral position. The converging walls are truncated and separated to provide space for the dorsal spinous processes and the width of the spline and has sufficient width that the weight of the animal is evenly distributed along its trunk to avoid distortion of its anatomy.

19 Claims, 3 Drawing Figures

RADIOGRAPHIC RACK APPARATUS FOR ANIMALS

BACKGROUND OF THE INVENTION

This invention relates generally to positioning aids for animals and more particularly to such aids useful for maintaining animals such as dogs and cats in a selected position while the animals are being subjected to radiographical procedures.

In taking X-rays of cats and dogs it is conventional to use a variety of positioning and restraining aids to ensure that the animals are maintained in a selected position for the time required to complete the radiographical procedure and so that the radiologists and technicians can remove themselves from the environs to avoid exposure to the radiation. These aids typically include, for example, sand bags, straps, foam blocks and tape. While it is possible to obtain satisfactory results using such means they all suffer from serious deficiencies. Many materials, such as sand, are radiodense and will cause artifact production thereby deleteriously affecting the results of the X-rays. The use of these aids also involves complex and time consuming routines of tying and stretching animals as well as the frequent contamination of the aids with often vile smelling excretions.

The most difficult position to maintain is the ventral dorsal view which is generally taken with the animal in the supine position. The combination of having the center of gravity several inches above the table's surface and the weight being blanced upon the dorsal spinous processes, skull and pelvis produces an inherently unstable position with the animal often leaning to a side thereby destroying the symmetry required to accurately read the radiograph. Although dorso ventral views, or sternal views, are generally easier to obtain because the fore and hind legs stabilize the position, deep chested dogs, such as the Borzoi, are not stable even in this position.

SUMMARY OF THE INVENTION

Among the several objects of the invention may be noted the provision of a simple yet effective positioning and restraining means usable with dogs and cats of various sizes and shapes both in the ventro dorsal and the dorso ventral positions which is radiographically transparent. Another object of the invention is the provision of such means which minimizes positioner induced distortion or deformation of the anatomy of the animal. Yet another object is the provision of a radiographical positioning and restraining rack for animals such as cats and dogs which is relatively inexpensive, durable, easily sanitizable and one which is conducive to efficient storage and is aesthetically pleasing. Still another object is the provision of a device for positioning and restraining animals which is useful with all breeds of dogs and cats.

Various additional objects and advantages of the present invention will become readily apparent from the following detailed description and accompanying drawings.

Briefly, the above objects are realized by providing a rack which is configured to form generally planar load support walls which downwardly converge toward one another and which have a nadir portion which is truncated to effectively lower the center of gravity of an animal received between the converging walls while providing space for the width of the spine and for the dorsal spinous processes of the vertebrae so that the significant portion of the weight of the animal is received on the load support walls rather than on the truncated nadir portion. The rack is formed sufficiently wide that positioner induced distortion or deformation of the animal is minimized, the width preferably being between four and six inches. The load support walls lie in planes which form an angle with one another selected to suit a skeletal class, approximately 60° for animals having a generally circular chest configuration and animals having generally oval chest configurations with chest widths in the order of two thirds of the spinous to sternal distance of the animals and approximately 45° for animals having generally elliptical chest configurations with chest widths in the order to half or less than the spinous to sternal distance of the animal.

The load bearing walls are supported by a pair of planar walls which in one embodiment extend generally parallel to one another and in another embodiment diverge in a downwardly direction in order to provide extra stability.

The rack is preferably integrally formed with the walls joined to one another through a radius selected on the basis of the type of material employed and its thickness, which in the case of acrylic, a preferred radiographically essentially transparent material, is slightly greater than three times its thickness.

An aperture may be provided in one of the walls to facilitate hanging of the rack on a support.

BRIEF DESCRIPTION OF THE DRAWINGS

In the accompanying drawings in which several of the preferred embodiments of the invention are illustrated.

Figure 1:
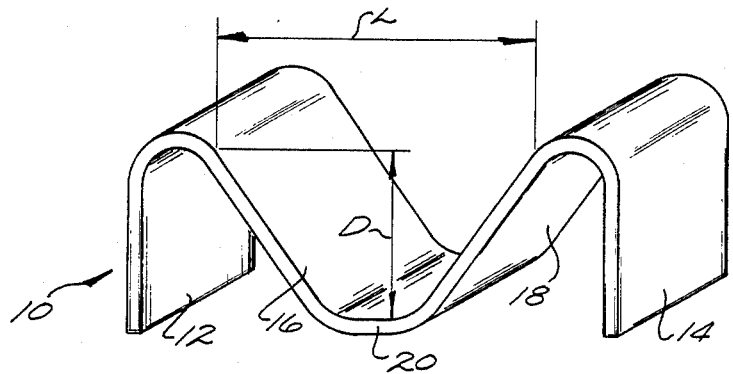
FIG. 1 is a perspective elevational view of a rack particularly useful with animals having a generally circular chest configuration made in accordance with the invention.

Dimensions of certain parts as shown in the drawings may have been modified or exaggerated for the purpose of clarity of illustration.

DESCRIPTION OF PREFERRED EMBODIMENTS

Turning now to the drawings, Numeral 10 refers generally to a rack particularly suited for animals of the skeletal class having in cross section a generally circular chest configuration. That is, these animals, which include most cats and smaller breeds of dogs, have a chest width which is very close to their vertebral-sternal distance and have a center of gravity that is almost in the center of the chest. When placed on their backs, they require support with a relatively wide base but not a high elevation.

Rack 10 is formed of radiographically transparent material, such as acrylic, having first and second planar walls 12 and 14 extending generally parallel to one another integrally connected respectively to third and fourth generally planar load support walls 16 and 18.

Walls 16 and 18 lie in respective planes which form an angle with each other of approximately 60° and have a nadir portion 20 which is truncated in order to effectively lower the center of gravity of an animal received between walls 16 and 18 while providing space for the width of the spine and for the spinous processes of the vertebrae so that the weight of the animal is supported primarily by the load support walls and not the nadir portion 20. The resultant rack provides stable support for this class of animals in either the ventral dorsal or dorsal ventral position by applying inward pressure along a line on either side of the trunk. The angle formed by walls 16 and 18 is such that the animal is snugly supported through the force of gravity acting through the support areas on walls 16 and 18.

Walls 12 and 14 are connected respectively to walls 16 and 18 and walls 16 and 18 are connected respectively to nadir portion 20 preferably through an equal radius chosen on the basis of the material employed for the rack and its thickness. In the case of acrylic, the radius is chosen to be equal to or slightly greater than three times the thickness.

A successful rack for animals of the circular chest configuration, as described above, was made of clear cast acrylic, having an overall height of 3 3/16 inches, a length of 8 inches, 3/16 inch thickness and an inside radius "R" of 19/32 inch. The truncated nadir portion was made wider to accommodate the vertebrae and spinous processes of the animals by spacing the center of the radius "R" for the walls 16 and 18 respectively $\frac{5}{8}$ inch apart with a smooth curve or even a generally planar central wall portion joining the two walls. The rack was formed with an open top end having a length "L" between walls 16 and 18 of 6⅜ inches and a depth "D" of 3 inches for a depth to length ratio of 0.49. The rack had a width of four inches in order to reduce positioner induced deformation of the anatomy of the animal by enabling the weight of the animal to be distributed along a significant portion of its trunk. Such deformation, or pinching of the body, is radiographically visible and deleteriously effects accurate reading of the radiograph. Additionally, the width of the rack has a direct bearing on the strength of the rack and its rigidity; however, in practice, the width is limited to avoid rendering the rack difficult to store and handle, while still providing the required support.

Figure 2:
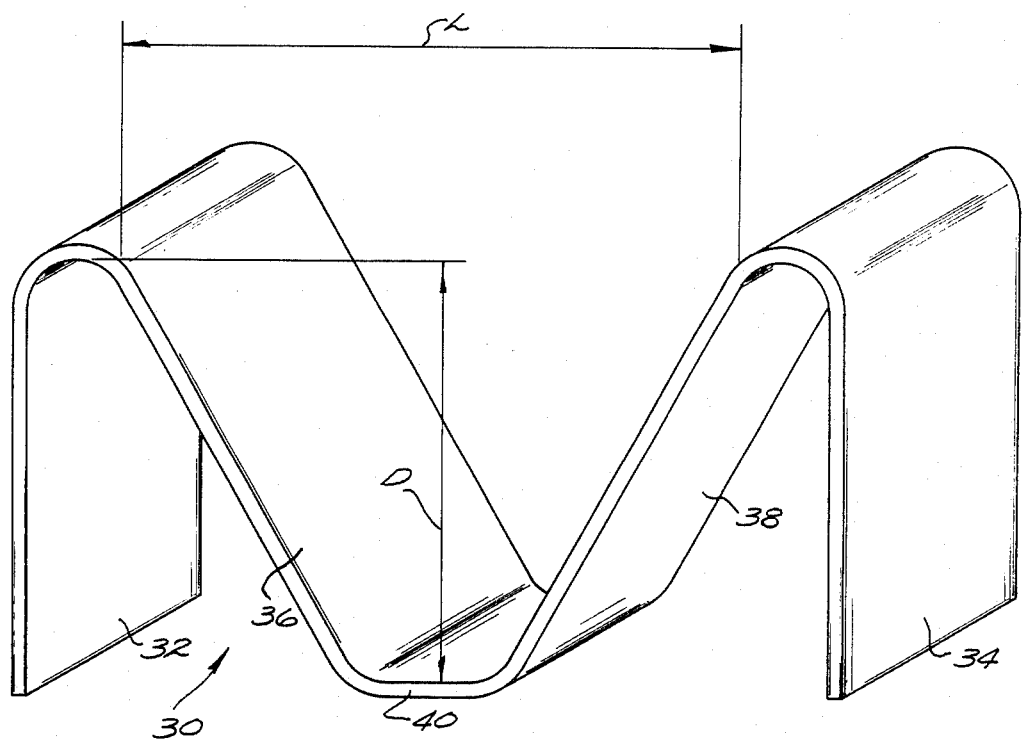
FIG. 2 is a view similar to FIG. 1 of a rack particularly useful with animals having a generally oval chest configuration made in accordance with the invention.

Rack 30, shown in FIG. 2, is configured to be particularly suited for animals of the skeletal class having in cross section a generally oval chest configuration. That is, the majority of dog breeds have rounded sternae and rib cages with a chest width approximately two-thirds of the spinous-sternal distance. Thus the center of gravity of this class of animals is relatively higher when placed on their backs and, therefore, requires wide based support with some elevation of the support points.

First and second planar walls 32, 34 extend generally parallel to one another and are integrally attached to respective third and fourth generally planar load support walls 36 and 38. As in the FIG. 1 embodiment the load support walls lie in respective planes which form an angle with each other of approximately 60° and have a truncated portion 40. Walls 32 and 34 are connected respectively to walls 36 and 38 and walls 36 and 38 are connected respectively to nadir portion 40 preferably through an equal radius, again related to the thickness of the material employed.

A successful rack for animals of the oval chest configuration, as described above, was made of cast acrylic, ¼ inch in thickness, having an overall height of 9 inches, a length of 14 inches, with an inside radius of 13/16 inch. The center of the radius "R" for walls 36 and 38 and their juncture with nadir portion 40 was spaced 1 inch apart. Length "L" of the open top end was 10¼ inches and its depth "D" was 6¾ inches for a depth to length ratio of 0.64. A width of 6 inches was found to provide adequate weight distribution of the animal along its trunk to reduce distortion of the anatomy.

Figure 3:
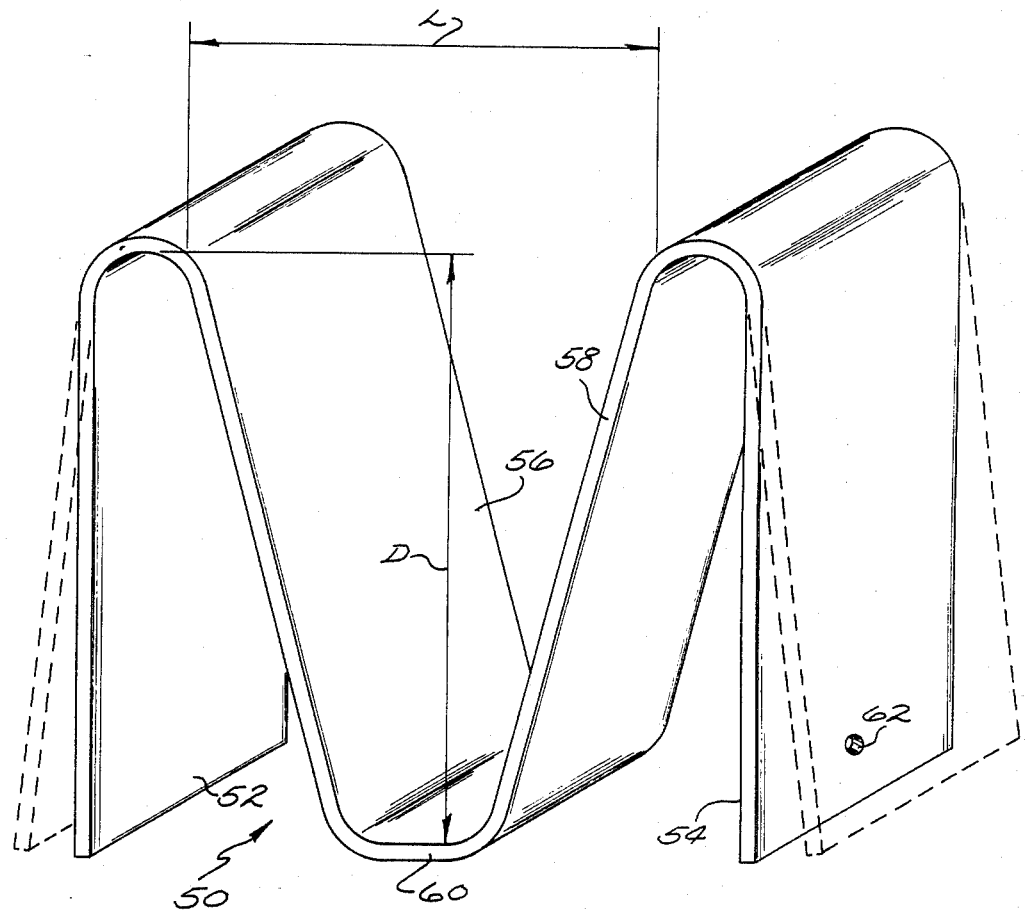
FIG. 3 is a view similar to FIGS. 1 and 2 of a rack particularly useful with animals having a generally elliptical chest configuration made in accordance with the invention.

Rack 50, shown in FIG. 3, is configured to be particularly suited for deep chested animals, such as Doberman Pinchers and Great Danes, of the skeletal class having in cross section generally elliptical chest configuration with a chest width that is generally less than one half of the spinous to sternal distance. A relatively high center of gravity when supine requires elevated support points but the narrowness of their chests requires narrower support bases.

First and second planar walls 52, 54 extend generally parallel to one another and are integrally attached to respective third and fourth generally planar load support walls 56, 58. Load support walls 56, 58 lie in respective planes which form an angle with each other of approximately 45° and have a truncated portion 60. Walls 52 and 54 are connected respectively to walls 56 and 58 and walls 56 and 58 are connected respectively to nadir portion 60 preferably through an equal radius, again related to the thickness of the material employed.

A successful rack for deep chested animals as described above was made of cast acrylic ¼ inch thick, having an overall height of 10¼ inches, a length of 11½ inches, with an inside radius of 13/16 inch. The center of the radius "R" for walls 56 and 58 and their junction with nadir portion 60 was spaced 1 inch apart. Length "L" of the open top end was 8 inches and its depth "D" was 10 inches for a depth to length ratio of 1.25. As in the FIG. 2 embodiment a width of six inches was found to be adequate to avoid deformation of the anatomy.

In order to facilitate storage an aperture 62 can be provided in one or both outer walls to enable the rack to be hung on a support. If additional stability of the rack is desired, particularly in the FIG. 3 embodiment in which the center of gravity of the supported animal is relatively high, the first and second walls can be configured to diverge in the downward direction as indicated by the dashed lines in FIG. 3.

Thermoplastic acrylic is a preferred material since it is easily formed into the desired configuration by heating using suitable strip heaters or the like, and subsequent molding, is essentially radiographically transparent (a ¼ inch sheet of acrylic absorbs approximately 4 KV of X-ray radiation, an amount which is not descernable for veterinary radiology), machines well, is relatively durable, has good rigidity and is relatively inexpensive. Although other materials, including polystyrene and polycarbonate can be utilized, they are generally less suitable than acrylic.

Although the invention has been described with respect to specific embodiments thereof, variations and modifications will become apparent to those skilled in the art. It is, therefore, the intention that the appended claims be interpreted as broadly as possible in view of the prior art to include all such variations and modifications.

I claim:

1. A positioning rack particularly useful with animals such as dogs and cats for maintaining a selected ventral dorsal or dorsal ventral position during radiological procedures formed of radiographically transparent material comprising
   support means, and
   a pair of sheets having a thickness "t" attached to the support means, each sheet forming a radius with the support means, the radius being at least three times "t", the sheets arranged to converge downwardly toward each other to provide a load support wall area on each sheet laterally aligned with each other, the convergent sheets having a nadir which is formed into a truncated portion to lower the center of gravity of an animal received in the rack while providing space for the width of the spine and for the spinous processes of the vertebrae of the animal with the load support walls spaced from one another such that the load of the animal is distributed primarily on the converging load support wall area and not the nadir in order to apply inward pressure on the animal along a line on either side of the trunk of the animal,
   the sheets having sufficient width to reduce positioner induced deformation of the anatomy of the animal by distributing the weight of the animal along a significant portion of the length of the animal.

2. A rack according to claim 1 in which the truncated portion is a smooth curved portion.

3. A rack according to claim 1 in which the truncated portion includes a generally planar portion.

4. A rack according to claim 1 particularly suited for animals of the class having in cross section a generally circular chest configuration and animals of the class having in cross section a generally oval chest configuration with chest widths in the order of two-thirds of the spinous to sternal distance of the animal in which the load support walls lie in respective planes which form an angle with each other of approximately 60°.

5. A rack according to claim 1 in which the rack is formed with an open end having a selected length between the converging sheets and the space between the converging sheets has a selected depth forming a depth to length ratio of approximately 0.49.

6. A rack according to claim 1 in which the rack is formed with an open end having a selected length between the converging sheets and the space between the converging sheets has a selected depth forming a depth to length ratio of approximately 0.64.

7. A rack according to claim 1 in which the rack is formed with an open end having a selected length between the converging sheets and the space between the converging sheets has a selected depth forming a depth to length ratio of approximately 1.25.

8. A rack according to claim 1 in which the width of the sheets is between approximately 4 and 6 inches.

9. A rack according to claim 5 in which the width of the sheets is approximately 4 inches.

10. A rack according to claim 6 in which the width of the sheets is approximately 6 inches.

11. A rack according to claim 7 in which the width of the sheets is approximately 6 inches.

12. A positioning rack particularly useful with animals such as dogs and cats for maintaining a selected ventral dorsal or dorsal ventral position during radiological procedures comprising
   a sheet of radiographically transparent material, the sheet formed so that it has first and second spaced outer walls respectively integrally connected to third and fourth generally planar load support walls downwardly converging toward one another and integrally connected together at a nadir portion, the nadir portion being formed into a truncated configuration to lower the center of gravity of an animal received in the rack while providing space for the width of the spine and for the spinous processes of the vertebrae of the animal with the load support walls spaced from one another such that the load of the animal is distributed primarily on the converging load support walls and not the nadir portion in order to apply inward pressure on the animal along a line on either side of the trunk of the animal, the first and second walls are connected to the respective third and fourth walls forming a radius R therewith and the truncated configuration is connected to the third and fourth walls forming a radius R therewith, the material being formed of acrylic having a selected thickness "t" and R being at least three times "t",
   the sheets having a sufficient width to reduce positioner induced deformation of the anatomy of the animal by distributing the weight of the animal along a significant portion of the length of the animal.

13. A rack according to claim 12 in which the centers of the radius of the connection of the truncated configuration with the third and fourth walls are spaced from one another.

14. A rack according to claim 12 in which an aperture is provided in at least one of the first and second walls to facilitate hanging of the rack on a support.

15. A rack according to claim 12 in which the first and second walls lie in respective planes which are generally parallel to one another.

16. A rack according to claim 12 in which the first and second walls having distal free ends and opposite ends lie in respective planes which diverge from one another in a downward direction so that the distal free ends of the walls are spaced further from one another than on their opposite ends.

17. A rack according to claim 12 particularly suited for animals of the class having in cross section generally circular cross section in which the load support walls form an angle with each other of approximately 60° and in which the space between the third and fourth walls has an opening at the top of the rack of a selected length and the space between the third and fourth walls has a selected depth forming a depth to length ratio of approximately 0.49.

18. A rack according to claim 12 particularly suited for animals of the class having in cross section a generally oval chest configuration with chest widths in the order of two-thirds of the spinous to sternal distance of the animal in which the load support walls lie in respective planes which form an angle with each other of approximately 60° and in which the space between the third and fourth walls has an opening at the top of the rack of a selected length and the space between the third and fourth walls has a selected depth forming a depth to length ratio of approximately 0.64.

19. A rack according to claim 12 particularly suited for animals of the class having in cross section a generally elliptical chest configuration with chest widths in the order of half or less than the spinous to sternal distance of the animal in which the load support walls lie in respective planes which form an angle with each other of approximately 45° and in which the space between the third and fourth walls has an opening at the top of the rack of a selected length and the space between the third and fourth walls has a selected depth forming a depth to length ratio of approximately 1.25.

* * * * *